United States Patent
Nalesnik et al.

[11] Patent Number: 6,103,674
[45] Date of Patent: Aug. 15, 2000

[54] OIL-SOLUBLE MOLYBDENUM MULTIFUNCTIONAL FRICTION MODIFIER ADDITIVES FOR LUBRICANT COMPOSITIONS

[75] Inventors: Theodore E. Nalesnik, Hopewell Junction; Cyril A. Migdal, Pleasant Valley, both of N.Y.

[73] Assignee: Uniroyal Chemical Company, Inc., Middlebury, Conn.

[21] Appl. No.: 09/268,130

[22] Filed: Mar. 15, 1999

[51] Int. Cl.$^7$ .................. C10M 133/00; C10M 135/00
[52] U.S. Cl. ............................ 508/334; 508/362
[58] Field of Search ................... 508/334, 362

[56] References Cited

U.S. PATENT DOCUMENTS

| | | | |
|---|---|---|---|
| 3,419,589 | 12/1968 | Larson et al. | 260/429 |
| 3,509,051 | 4/1970 | Farmer et al. | 252/33.6 |
| 3,541,014 | 11/1970 | Le Suer | 252/49.7 |
| 4,098,705 | 7/1978 | Sakurai et al. | 252/33.6 |
| 4,164,473 | 8/1979 | Coupland et al. | 252/32.7 |
| 4,192,757 | 3/1980 | Brewster | 252/32.7 |
| 4,259,194 | 3/1981 | deVries et al. | 252/46.4 |
| 4,259,195 | 3/1981 | King et al. | 252/49.7 |
| 4,263,152 | 4/1981 | King et al. | 252/46.4 |
| 4,265,773 | 5/1981 | deVries et al. | 252/46.4 |
| 4,266,945 | 5/1981 | Karn | 44/68 |
| 4,269,606 | 5/1981 | Bonazza et al. | 44/63 |
| 4,272,387 | 6/1981 | King et al. | 252/46.4 |
| 4,283,295 | 8/1981 | deVries et al. | 252/46.4 |
| 4,285,822 | 8/1981 | deVries et al. | 252/46.4 |
| 4,289,635 | 9/1981 | Schroeck | 252/32.7 |
| 4,315,826 | 2/1982 | Schlicht et al. | 252/46.4 |
| 4,344,771 | 8/1982 | Bonazza et al. | 44/63 |
| 4,357,149 | 11/1982 | West et al. | 44/68 |
| 4,369,119 | 1/1983 | deVries et al. | 252/42.7 |
| 4,370,246 | 1/1983 | deVries et al. | 252/46.4 |
| 4,392,966 | 7/1983 | Schlicht | 252/32.7 |
| 4,394,279 | 7/1983 | deVries et al. | 252/46.4 |
| 4,395,343 | 7/1983 | deVries et al. | 252/32.7 |
| 4,402,840 | 9/1983 | deVries et al. | 252/45 |
| 4,414,122 | 11/1983 | West et al. | 252/49.7 |
| 4,428,848 | 1/1984 | Levine et al. | 252/32.7 |
| 4,466,901 | 8/1984 | Hunt et al. | 252/32.7 |
| 4,474,673 | 10/1984 | Hunt et al. | 252/42.7 |
| 4,479,883 | 10/1984 | Shaub et al. | 252/32.7 |
| 4,500,439 | 2/1985 | West et al. | 252/46.4 |
| 4,501,678 | 2/1985 | Katayama et al. | |
| 4,504,280 | 3/1985 | Efner et al. | 44/63 |
| 4,505,725 | 3/1985 | Schuettenberg | 44/66 |
| 4,505,835 | 3/1985 | Sung et al. | 252/51.5 |
| 4,639,255 | 1/1987 | Schuettenberg et al. | 44/62 |
| 4,647,389 | 3/1987 | Karol et al. | 252/51.5 |
| 4,765,918 | 8/1988 | Love et al. | 252/46.4 |
| 4,849,119 | 7/1989 | Horodysky | 252/51.5 |
| 4,889,647 | 12/1989 | Rowan et al. | 252/42.7 |
| 4,921,624 | 5/1990 | Kammann, Jr. | 252/48.6 |
| 4,957,651 | 9/1990 | Schwind | 252/56 |
| 4,990,656 | 2/1991 | Bresson et al. | 562/27 |
| 4,995,996 | 2/1991 | Coyle et al. | 252/42.7 |
| 5,143,633 | 9/1992 | Gallo et al. | 252/18 |
| 5,154,844 | 10/1992 | Perozzi | 252/47.5 |
| 5,164,102 | 11/1992 | Everett et al. | 252/32.7 |
| 5,338,471 | 8/1994 | Lal | 252/56 |
| 5,399,275 | 3/1995 | Lange et al. | 252/49 |
| 5,413,725 | 5/1995 | Lal et al. | 252/18 |
| 5,464,549 | 11/1995 | Sieberth | 252/51.5 |
| 5,498,355 | 3/1996 | Perozzi et al. | 252/49.6 |
| 5,498,809 | 3/1996 | Emert et al. | 585/13 |
| 5,631,213 | 5/1997 | Tanaka et al. | 508/363 |
| 5,650,381 | 7/1997 | Gatto et al. | 508/364 |
| 5,705,722 | 1/1998 | Monnier et al. | 585/240 |
| 5,736,491 | 4/1998 | Patel et al. | 508/365 |
| 5,840,672 | 11/1998 | Gatto | 508/334 |

FOREIGN PATENT DOCUMENTS 0 719 313 B1  9/1994  European Pat. Off. ..... C10M 141/08

*Primary Examiner*—Margaret Medley
*Assistant Examiner*—Cephia D. Toomer
*Attorney, Agent, or Firm*—Raymond D. Thompson; Paul Grandinetti

[57] ABSTRACT

A lubricating oil additive is disclosed that comprises the reaction product of:

(a) an unsaturated or saturated ester or acid,
(b) a diamine of the formula:

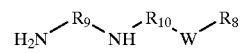

(c) carbon disulfide, and
(d) a molybdenum compound, wherein $R_8$ is an alkyl group of 1 to 40 carbon atoms, $R_9$ and $R_{10}$ are independently selected aliphatic or aromatic moieties, W is oxygen, sulfur, or —$CH_2$—. The additive imparts friction modification and beneficial antiwear, extreme pressure, and oxidation stability properties to the lubricating oil.

21 Claims, No Drawings

OIL-SOLUBLE MOLYBDENUM MULTIFUNCTIONAL FRICTION MODIFIER ADDITIVES FOR LUBRICANT COMPOSITIONS

BACKGROUND OF THE INVENTION

1. Field of the Invention

This invention relates to organo molybdenum derivatives and their use as multifunctional friction modifier, antiwear, extreme pressure, antioxidant additives for lubricants. The additives of the present invention are reaction products of mono- or poly-functional organic acids or esters and an aliphatic diamine that are further reacted with carbon disulfide and then with molybdenum compounds to form the final complex products.

2. Description of Related Art

Regulatory agencies today are seeking to improve the fuel economy of motor vehicles through legislation (CAFE requirements) that puts the responsibility for achieving such economy on the motor vehicle manufacturers, who in turn transfer at least a portion of this responsibility to lubricant oil manufacturers by means of engine oil specifications. As these fuel economy requirements become more and more rigorous, it becomes more and more important to incorporate friction modifier additives into lubricant compositions. Thus it is an object of the present invention to provide a friction modifier additive that imparts a reduction in the coefficient of friction of a lubricant composition.

In addition, zinc dialkyldithiophosphates (ZDDP) have been used in formulated oils as antiwear and antioxidant additives for more than 50 years. However, zinc dialkyldithiophosphates give rise to ash, which contributes to particulate matter in automotive exhaust emissions. Regulatory agencies are seeking to reduce emissions of zinc into the environment. Moreover, the phosphorus present in the dialkyldithiophosphates is also suspected of limiting the service life of catalytic converters that are used on vehicles to reduce pollution. It is important to limit the particulate matter and pollution formed during engine use for toxicological and environmental reasons, but it is also important to maintain undiminished the antiwear and antioxidant properties of the lubricating oil. In view of the aforementioned shortcomings with the known zinc- and phosphorus-containing additives, it is a further object of this invention to provide antiwear and antioxidant additives that contain neither zinc nor phosphorus.

In developing lubricating oils, there have been many attempts to provide additives that impart antifrictional or oiliness properties. Molybdenum compounds are known to be useful as friction modifiers and antioxidants and to be capable of providing antiwear and extreme pressure resistance properties in lubricating oil compositions.

Thiocarbamate additives for lubricating oils, particularly molybdenum-containing thiocarbamates, have been disclosed in the patent literature.

U.S. Pat. No. 3,419,589 discloses a process for the preparation of molybdenum (VI) dialkyldithiocarbamate complexes and sulfurized derivatives thereof in substantially high yields by the dilute nitric acid acidification of alkali dialkyldithiocarbamates and alkali molybdates and the subsequent treatment thereof with hydrogen sulfide to form the sulfurized derivatives of the reaction product. These compounds are said to be useful as additives for lubricants.

U.S. Pat. No. 3,509,051 discloses lubricating oils and greases that are said to exhibit excellent extreme pressure, antioxidant, and wear properties when they contain sulfurized oxymolybdenum dithiocarbamates of the general formula: $[R_2N-CS-S-]_2Mo_2O_mS_n$, where m+n=4, m is in the range of 2.35 to 3, n is in the range of 1.65 to 1, and R is a hydrocarbon group having 1 to 24 carbon atoms.

U.S. Pat. No. 3,541,014 discloses lubricant compositions that are said to have improved extreme pressure capabilities and antiwear properties, which are characterized by the presence therein of oil-soluble molybdenum-containing organic complexes. These complexes are produced by contacting molybdenum-containing anions with oil-soluble overbased, Group II metal-containing compositions until a portion of the anions reacts with the Group II metal. Lubricating oils, cutting oils, greases, and the like are illustrative of the lubricant compositions disclosed.

U.S. Pat. No. 4,098,705 discloses a compound of the formula:

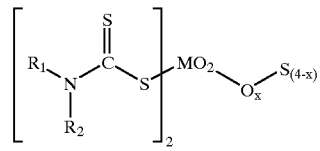

wherein $R_1$ and $R_2$ stand for a hydrocarbyl group having 1 to 24 carbon atoms and x is a number of 0.5–2.3 that is said to be useful as an additive for lubricants.

U.S. Pat. No. 4,164,473 discloses hydrocarbon-soluble organo molybdenum complexes obtained as the reaction product of a hydrocarbyl substituted hydroxy alkylated amine, e.g., N,N',N'-tris(2-hydroxy ethyl)-n-tallow-1,3-diaminopropane, with about one molar equivalent of a molybdenum compound, e.g., ammonium molybdate, that are said to be useful hydrocarbon additives particularly in combination with an oil-soluble sulfur donor, e.g., a metal dialkyl dithiophosphate to provide an additive combination for lubricating oils. Lubricating compositions comprising these coadditives are disclosed to exhibit improved antifriction and antiwear properties.

U.S. Pat. No. 4,259,194 discloses antioxidant additives for lubricating oil that are prepared by combining ammonium tetrathiomolybdate and a basic nitrogen compound complex to form a sulfur- and molybdenum-containing composition.

U.S. Pat. No. 4,259,195 discloses antioxidant additives for lubricating oil that are prepared by combining a polar promoter, an acidic molybdenum compound, and certain basic nitrogen compounds to form a molybdenum-containing composition.

U.S. Pat. No. 4,265,773 discloses antioxidant additives for lubricating oil that are prepared by combining an acidic molybdenum compound, an oil-soluble basic nitrogen compound, and carbon disulfide to form a sulfur- and molybdenum-containing composition.

U.S. Pat. No. 4,266,945 discloses the preparation of molybdenum-containing compositions by the reaction of an acid of molybdenum or a salt thereof, phenol or aldehyde condensation product therewith, and a primary or secondary amine. The preferred amines are diamines such as tallow-substituted trimethylene diamine and their formaldehyde condensation products. An optional but preferred ingredient in the reaction mixture is at least one oil-soluble dispersant. The molybdenum-containing compositions are said to be useful as additives in fuels and lubricants, especially so in lubricants when combined with compounds containing active sulfur.

U.S. Pat. No. 4,272,387 discloses antioxidant additives for lubricating oil that are prepared by combining an acidic molybdenum compound, a basic nitrogen compound complex, and a sulfur source to form a sulfur- and molybdenum-containing composition.

U.S. Pat. No. 4,283,295 discloses antioxidant additives for lubricating oil that are prepared by combining a polar promoter, ammonium tetrathiomolybdate, and a basic nitrogen compound complex to form a sulfur- and molybdenum-containing composition.

U.S. Pat. No. 4,285,822 discloses antioxidant additives for lubricating oil that are prepared by (1) combining a polar solvent, an acidic molybdenum compound, and an oil-soluble basic nitrogen compound to form a molybdenum-containing complex and (2) contacting said complex with carbon disulfide to form a sulfur- and molybdenum-containing composition.

U.S. Pat. No. 4,289,635 discloses molybdenum-containing compositions that are prepared by reacting an olefinically unsaturated compound capable of reacting with active sulfur with a composition prepared by reacting:

(a) a phosphorus-containing acid represented by the formula:

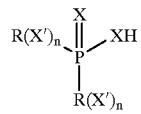

wherein each X and X' is independently oxygen or sulfur, each n is zero or one and each R is independently the same or a different hydrocarbon-based radical; and
(b) at least one hexavalent molybdenum oxide compound, and
(c) hydrogen sulfide, in the presence of
(d) a polar solvent. It is said that the compositions are useful as additives for lubricants and that internal combustion engines exhibit improved fuel economy when lubricated with them.

U.S. Pat. No. 4,315,826 discloses multipurpose lubricant additives that are prepared by reaction of carbon disulfide with thiomolybdenum derivatives of polyalkenylsuccinimides having basic nitrogen functions. It is said that the subject additives function as dispersants possessing excellent antifriction properties and impart antiwear and antioxidant properties to a lubricant.

U.S. Pat. No. 4,369,119 discloses antioxidant additives for lubricating oil that are prepared by combining (a) a sulfur-containing molybdenum compound prepared by reacting an acidic molybdenum compound, a basic nitrogen compound, and a sulfur compound, with (b) an organic sulfur compound.

U.S. Pat. No. 4,395,343 discloses antioxidant additives for lubricating oil that are prepared by combining (a) a sulfur containing molybdenum compound prepared by reacting an acidic molybdenum compound, a basic nitrogen compound, and carbon disulfide, with (b) an organic sulfur compound.

U.S. Pat. No. 4,402,840 discloses antioxidant additives for lubricating oil that are prepared by combining (a) a sulfur containing molybdenum compound prepared by reacting an ammonium thiomolybdate compound, and a basic nitrogen compound, with (b) an organic sulfur compound.

U.S. Pat. No. 4,474,673 discloses antifriction additives for lubricating oil that are prepared by reacting a sulfurized organic compound having an active hydrogen or potentially active hydrogen with a molybdenum halide.

U.S. Pat. No. 4,479,883 discloses a lubricating oil composition that is said to have particularly improved friction reducing properties that comprises an ester of a polycarboxylic acid with a glycol or glycerol and a selected metal dithiocarbamate and that contains a relatively low level of phosphorus.

U.S. Pat. No. 4,501,678 discloses a lubricant containing molybdenum dialkyldithiocarbamates that is said to be useful for improving the fatigue life of gears.

U.S. Pat. No. 4,765,918 discloses a lubricating oil additive prepared by reacting a triglyceride with a basic nitrogen compound to form a reaction product, reacting the reaction product with an acidic molybdenum compound to form an intermediate reaction product, and reacting the intermediate reaction product with a sulfur compound.

U.S. Pat. No. 4,889,647 discloses molybdenum complexes prepared by reacting (a) a fatty oil, (b) diethanolamine, and (c) a molybdenum source. The complexes are said to impart antifriction and antiwear properties to lubricating compositions and to decrease fuel consumption in internal combustion engines.

U.S. Pat. No. 4,995,996 discloses a lubricating composition comprising a major amount of an oil of lubricating viscosity and a minor amount of an additive having the formula $Mo_2L_4$ wherein L is a ligand selected from xanthates and mixtures thereof and, in particular, xanthates having a sufficient number of carbon atoms to render the additive soluble in the oil. In general, the xanthate ligand, L, will have about 2 to 30 carbon atoms.

SUMMARY OF THE INVENTION

The present invention provides a lubricating oil organo molybdenum additive that imparts friction modification and antiwear, extreme pressure, and antioxidant properties to a lubricating oil. To form the additive, a mono- or polyfunctional organic acid or ester and an aliphatic diamine are reacted to form an organic ligand, which is further reacted with carbon disulfide and then with a molybdenum compound.

More particularly, the present invention is directed to a lubricating oil additive comprising the reaction product of
(a) an unsaturated or saturated ester or acid,
(b) a diamine of the formula:

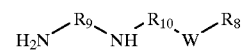

(c) carbon disulfide, and
(d) a molybdenum compound,
wherein $R_8$ is an alkyl group of 1 to 40 carbon atoms, $R_9$ and $R_{10}$ are independently selected aliphatic or aromatic moieties, W is oxygen, sulfur, or —$CH_2$—.

In another aspect, the present invention is directed to a lubricating composition comprising a lubricating oil and an additive comprising the reaction product of
(a) an unsaturated or saturated ester or acid,
(b) a diamine of the formula:

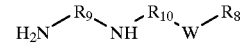

(c) carbon disulfide, and
(d) a molybdenum compound,
wherein $R_8$ is an alkyl group of 1 to 40 carbon atoms, $R_4$, and $R_{10}$ are independently selected aliphatic or aromatic moieties, W is oxygen, sulfur, or —$CH_2$—.

DESCRIPTION OF THE PREFERRED EMBODIMENT

The additive of the present invention is a reaction product of monap or polyfunctional organic acids or ester s and an aliphatic diamine, which is further reacted with carbon disulfide and then with a molybdenum compound to form the lo final complex product.

The mono- or polyfunctional organic acids or esters used to form the reaction product are of the formula:

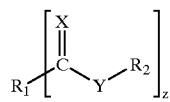

wherein $R_1$ is a hydrocarbon moiety of 1 to 44, preferably 1 to 12, carbon atoms, either straight chain or branched chain or cyclic, saturated or unsaturated, $R_2$ is hydrogen, a hydrocarbon radical, or a functionalized hydrocarbon radical, preferably having 1 to 18 carbon atoms, Z is an integer of 1 to 5, preferably 1 to 4, and X and Y are independently selected from the group consisting of sulfur and oxygen.

In the above structural formula, $R_1$ is a fully saturated or a partially unsaturated alkyl moiety of 1 to 44 carbon atoms and can have either a straight chain or a branched chain. Thus $R_1$ can, for example, be methyl, ethyl, propyl, butyl, pentyl, hexyl, 2-ethyl hexyl, heptyl, octyl, nonyl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, tetracosyl, pentacosyl, triacontyl, pentatriacontyl, tetracontyl, and the like, and isomers and mixtures thereof. Additionally, contained within the chains of $R_1$ may be ester groups or heteroatoms, such as oxygen and sulfur, which may take the form of ethers, poly ethers, and/or sulfides.

Accordingly, representative acids that can be used in the practice of the present invention include monobasic acids such as acetic, propionic, butyric, hexanoic, oleic, myristic, and the like and dibasic acids such as malonic, succinic, glutaric, adipic, pimelic, suberic, azelaic, sebacic, and the like.

Those skilled in the art will understand that either acids or esters can be used in the practice of the present invention. Where esters are employed, they will be derived from such acids as are described above, or the anhydrides thereof, by reaction with an appropriate alcohol, which term as employed herein is intended to include thiols.

The mono- or polyfunctional organic alcohols used to prepare the esters from the acids have the formula:

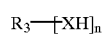

wherein $R_3$ is a fully saturated or partially unsaturated hydrocarbon moiety of 1 to 44 carbon atoms, preferably 1 to 12 carbon atoms, more preferably 1 to 9 carbon atoms, either straight chain or branched chain or cyclic, n is an integer of 1 to 10, preferably 1 to 4, and X is sulfur or oxygen. $R_3$ can, for example, be methyl, ethyl, propyl, butyl, pentyl, hexyl, 2-ethyl hexyl, heptyl, octyl, nonyl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, tetracosyl, pentacosyl, triacontyl, pentatriacontyl, tetracontyl, and the like and isomers and mixtures thereof. Additionally, ester groups or heteroatoms such as oxygen, sulfur, and nitrogen, which may take the form of ethers, polyethers, sulfides, or amines, can be contained within the $R_3$ chain. Moreover, the alcohol as described by the structure can be a diol such as ethylene glycol or an alkanediol such as propanediol. Further, triols such as glycerol and tetraols such as pentaerythritol can be used to prepare the esters employed in the practice of the present invention.

Esters useful in the practice of this invention include but are not limited to ethylene glycol dioleate, propylene glycol dioleate, butanediol dioleate, glycerol monooleate, glycerol linoleate, glycerol linolenate, glycerol trioleate, pentaerythritol tetraoleate, pentaerythritol trioleate monomyristate, trimethylol propane trioleate, trimethylol propane dioleate monomyristate, trimethylol propane dilinoleate monooleate, and the like, and dibasic esters, such as dioleyl adipate, dioleyl sebacate, dioleyl maleate, dioleyl succinate, dilinoleyl adipate, and the like. Mixtures of such esters, and others similar thereto, are also useful.

One preferred raw material source that is both inexpensive and plentiful is vegetable oil. Another preferred raw material is synthetic vegetable oil. Vegetable oil is a mixture of triglycerides, and synthetic vegetable oil may be a mixture of mono-, di-, and triglycerides of the formula:

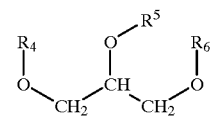

where $R_4$, $R_5$, $R_6$ comprise hydrogen or a hydrocarbon radical having the formula:

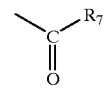

and where $R_7$ is a $C_6$ to $C_{24}$ hydrocarbon moiety, with the proviso that no more than two of $R_4$, $R_5$, $R_6$ can be hydrogen.

These mixtures can be naturally occurring, e.g., canola oil (rapeseed oil), corn oil, coconut oil, sunflower oil, soybean oil, lard, palm oil, etc., or can be synthesized by reaction of glycerol with fatty acids, e.g., oleic acid, linoleic acid, linolenic acid, etc. The preferred vegetable oil for use in the practice of the present invention is canola oil. Although we describe synthetic vegetable oil as a mixture of mono-, di-, and triglycerides, pure mono-, di-, and triglycerides would be effective as well.

In the practice of the present invention, amines are reacted with the above-described acids or esters, preferably vegetable oils, to form an intermediate. Such amines are exemplified by the formula:

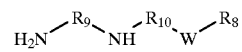

wherein $R_8$ is an alkyl group of 1 to 40 carbon atoms, $R_9$ and $R_{10}$ are independently selected aliphatic or aromatic moieties, and W is oxygen, sulfur, or $-CH_2-$.

In the above structural formula, $R_8$ is an alkyl moiety of 1 to 40, preferably 8 to 24, carbon atoms and can have either a straight chain or a branched chain, a fully saturated or partially unsaturated hydrocarbon chain, e.g., methyl, ethyl, propyl, butyl, pentyl, hexyl, 2-ethyl hexyl, heptyl, octyl, nonyl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, tetracosyl, pentacosyl, triacontyl, pentatriacontyl, tetracontyl, and the like, and isomers and mixtures thereof. Additionally, $R_8$ can contain within its chain ester groups or heteroatoms such as oxygen and sulfur which can take the form of ethers, polyethers, and/or sulfides.

$R_9$ and $R_{10}$ in the above formula, independently, can be aliphatic or aromatic moieties. They are preferably aliphatic, more preferably alkylene, and most preferably alkylene of two or three carbon atoms, i.e., ethylene, propylene, or isopropylene. Of the latter, it is preferred that $R_9$ and $R_{10}$ be independently selected from the group consisting of ethylene ($—CH_2CH_2—$) and propylene ($-CH_2CH_2CH_2—$). It is especially preferred that $R_9$ and $R_{10}$ be the same and that they both be propylene.

The following is a list of representative ether polyamines commercially available from Tomah Inc. that can be used to react with vegetable oil or other saturated or unsaturated esters or acids, and then treated with carbon disulfide and molybdenum compounds to form the products of the present invention:

DA-1214 (Octyl/decyloxypropyl-1,3-diaminopropane),
DA-14 (Isodecyloxypropyl-1,3-diaminopropane),
DA-16 (Isododecyloxypropyl-1,3-diaminopropane),
DA-1618 (Dodecyl/tetradecyloxypropyl-1,3-diaminopropane),
DA-17 (Isotridecyloxypropyl-1,3-diaminopropane), and
DA-18 (Tetradecyloxypropyl-1,3-diaminopropane).

The following is a partial list of polyamines commercially available from Akzo Nobel Chemicals Inc. that can also be used to react with vegetable oil or other saturated or unsaturated esters or acids, and then treated with carbon disulfide and molybdenum compounds to form the products of the present invention:

Duomeen C (N-coco-1,3-diaminopropanes),
Duomeen T (N-tallow-1,3-diaminopropanes), and
Duomeen OL (N-oleyl-1,3-diaminopropane).

In the practice of the present invention, it is preferred that the diamine be used in a concentration of about 10 weight percent to about 70 weight percent.

The suitable sulfur compound to react with the intermediate diamine and ester or acid reaction product is carbon disulfide.

Suitable molybdenum compounds useful in the practice of the present invention include molybdic acid, ammonium molybdate, and molybdenum salts such as $MoOCl_4$, $MoO_2Br_2$, $Mo_2O_3C_4$, and $MoO_3$, and their thio analogues such as $MoS_3$ and $(NH_4)_2MoS_4$. The preferred molybdenum compound is molybdenum trioxide. It is preferred in the practice of the present invention that the molybdenum compound be used in a concentration of about 0.01 to about 15 weight percent.

The process for making the molybdenum-based friction modifiers of the present invention can, if desired, be carried out in a single reaction vessel and requires no solvent, isolation of intermediate products, or removal of reaction solvent or reaction byproducts (Examples 13 through 19). It results in a clear liquid product with a very desirable color, which is light yellow to orange at the typical 1.0 weight percent dosage levels used in petroleum and synthetic lubricant base oils. Most other commercial molybdenum friction modifiers impart undesirable green, blue, and purple colors to finished fully formulated crank case motor oils.

The process is initiated by charging the reactor, under a nitrogen blanket, with the starting vegetable oil. Typical glyceride vegetable oils used are based on $C_{12}$ to $C_{22}$ fatty acids, both saturated and unsaturated. These vegetable oils can be, for example, canola (rapeseed), corn, soya, peanut, sunflower, cottonseed, olive, safflower, or coconut oils. Mixtures of these or similar oils can also be used. Next a diamine is charged. In the diamine, one amine group must be a primary amine and the other amine group must be a secondary amine. The amine groups are separated by a branched or linear $C_1$ to $C_{10}$ aliphatic or aromatic moiety. The mole ratio of the diamine to the vegetable oil is typically in the range of 0.5 to 2.0. This reaction to medium is heated to a temperature in the range of 110° to 150° C. for three to ten hours depending on the reactivity of the diamine to form a reaction intermediate, which, where vegetable oil is used, is a mixture of fatty acid amide and the mono and/or diacid glycerides. The reaction medium is then cooled to room temperature, whereupon carbon disulfide is added slowly under a nitrogen blanket. The reaction medium will exotherm. Molybdenum trioxide is then added to the reaction medium. The reaction temperature is raised to 80° to 105° C. for 30 to 60 minutes, then to 135° C. for one to six hours under a nitrogen blanket. The reaction product is cooled to 60° to 90° C. and filtered (if needed) through a bed of Celite filter aid. Alternatively, the product can be diluted with a hydrocarbon solvent and filtered, after which the solvent is removed under vacuum. The final product is a dark, reddish-brown liquid that imparts a light yellow to orange color to a petroleum base oil at 1.0 to 1.5 weight percent dosage levels. The molybdenum incorporated in the product can range from 2 to 8 weight percent.

The additives of the present invention can be used in combination with other additives typically found in lubricating oil, as well as with other friction modifier additives. Typical additives found in lubricating oils are dispersants, detergents, corrosion/rust inhibitors, antioxidants, e.g., secondary amine antioxidants, hindered phenolic antioxidants, sulfur-containing hindered phenolic antioxidants, sulfurized olefins, thiadiazoles, antiwear agents, e.g., zinc dialkyldithiophosphates, antifoamants, friction modifiers, seal swell agents, demulsifiers, VI improvers, and pour point depressants. See, for example, U.S. Pat. No. 5,498,809, incorporated herein by reference, for a description of useful lubricating oil composition additives.

Examples of dispersants include polyisobutylene succinimides, polyisobutylene succinate esters, Mannich Base ashless dispersants, and the like. Examples of detergents include metallic phenates, metallic sulfonates, metallic salicylates, and the like. Examples of friction modifiers that can be used in combination with the friction modifiers of the present invention include fatty acid esters and amides, organo molybdenum compounds, molybdenum dialkylthiocarbamates, molybdenum dialkyl dithiophosphates, and the like. An example of an antifoamant is polysiloxane, and the like. An example of a rust inhibitor is polyoxyalkylene polyols, and the like. Examples of VI improvers include olefin copolymers and dispersant olefin copolymers, and the like. An example of a pour point depressant is poly(methyl methacrylate), and the like.

Examples of antioxidant additives that can be used in combination with the additives of the present invention include alkylated diphenylamines and N-alkylated phenylenediamines. Secondary diarylamines are well known antioxidants and there is no particular restriction on the type of secondary diarylamine that can be used in the practice of the present invention. The secondary diarylamine type of antioxidant in a lubricating oil provides a synergistic antioxidant mixture with the additive of the present invention. Preferably, the secondary diarylamine antioxidant is of the general formula $R_{11}$—NH—$R_{12}$, where $R_{11}$ and $R_{12}$ each independently represent a substituted or unsubstituted aryl group having 6 to 46 carbon atoms. Illustrative of substituents for the aryl group are aliphatic hydrocarbon groups such as alkyl having 1 to 40 carbon atoms, hydroxyl, carboxyl, amino, N-alkylated amino, N',N-dialkylated amino, nitro, or cyano. The aryl is preferably substituted or unsubstituted phenyl or naphthyl, particularly where one or both of the aryl groups are substituted with alkyl such as one having 4 to 24 carbon atoms.

The alkyl moiety of 1 to 40 carbon atoms can have either a straight or a branched chain, which can be either a fully saturated or a partially unsaturated hydrocarbon chain, e.g., methyl, ethyl, propyl, butyl, pentyl, hexyl, 2-ethyl hexyl, heptyl, octyl, nonyl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, tetracosyl, pentacosyl, tricontyl, pentatriacontyl, tetracontyl, and the like, and isomers and mixtures thereof.

Examples of some secondary diarylamines that can be employed in the practice of the present invention include: diphenylamine, dialkylated diphenylamine, trialkylated diphenylamine, or mixtures thereof, 3-hydroxydiphenylamine, 4-hydroxydiphenylamine, N-phenyl-1,2-phenylenediamine, N-phenyl-1,4-phenylenediamine, mono- and/or di-butyldiphenylamine, mono- and/or di-octyldiphenylamine, mono- and/or di-nonyldiphenylamine, phenyl-α-naphthylamine, phenyl-β-naphthylamine, di-heptyldiphenylamine, mono- and/or di-(α-methylstyryl)diphenylamine, mono- and/or di-styryldiphenylamine, N,N'-diisopropyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethylbutyl)-N'-phenyl-p-phenylenediamine, N-('-methylpentyl)-N'-phenyl-p-phenylenediamine, N-cyclohexyl-N'-phenyl-p-phenylenediamine, 4-(p-toluenesulfonamido) diphenylamine, 4-isopropoxydiphenylamine, tert-octylated N-phenyl-1-naphthylamino, and mixtures of mono- and dialkylated t-butyl-t-octyldiphenylamines.

Another example of the antioxidant types that can be used in combination with the additives of the present invention is the hindered phenolic type. The hindered phenolic type of antioxidant may provide a synergistic antioxidant mixture with the additives of the present invention in a lubricating oil. As illustrative of oil soluble phenolic compounds, may be listed alkylated monophenols, alkylated hydroquinones, hydroxylated thiodiphenyl ethers, alkylidenebis phenols, benzyl compounds, acylaminophenols, and esters and amides of hindered phenol-substituted alkanoic acids.

Examples of useful phenolic antioxidants include:
2,6-di-t-butyl-4-methylphenol,
2,6-di-t-butylphenol,
2-t-butyl-4,6-dimethylphenol,
2,6di-t-butyl-4-ethylphenol,
2,6di-t-butyl-4-n-butylphenol,
2,6-di-t-butyl-4-isobutylphenol,
2,6-dicyclopentyl-4-methylphenol,
2-(α-methylcyclohexyl)-4,6-dimethylphenol,
2,6-dioctadecyl-4-methylphenol,
2,4,6-tricyclohexylphenol,
2,6-di-t-butyl-4-methoxymethylphenol,
o-t-butylphenol,
2,5-di-t-butyl-hydroquinone,
2,5-di-t-amyl-hydroquinone,
2,6-di-phenyl-4-octadecyloxyphenol,
2,2'-thiobis(6-t-butyl-4-methylphenol)
2,2'-thiobis(4-octylphenol),
4,4'-thiobis(6-t-butyl-3-methylphenol),
4,4'-thiobis(6-t-butyl-2-methylphenol),
2,2'-methylenebis(6-t-butyl-4-methylphenol),
2,2'-methylenebis(6-t-butyl-4-ethylphenol),
2,2'-methylenebis{4-methyl-6-(α-methylcyclohexyl)phenol},
2,2'-methylenebis(4-methyl-6-cyclohexylphenol),
2,2'-methylenebis(6-nonyl-4-methylphenol),
2,2'-methylenebis(4,6-di-t-butylphenol),
2,2'-methylidenebis(4,6-di-t-butylphenol),
2,2'-ethylidenebis(6-t-butyl-4-isobutylphenol),
2,2'-methylenebis{(6-α-methylbenzyl)-4-nonylphenol},
2,2'-methylenebis{6-(α,α-dimethylbenzyl)-4-nonylphenol},
4,4'-methylenebis(4,6-di-t-butylphenol),
4,4'-methylenebis(6-t-butyl-2-methylphenol),
1,1-bis(5-t-butyl-4-hydroxy-2-methylphenyl)butane,
2,6-di(3-t-butyl-5-methyl-2-hydroxybenzyl)-4-methylphenol,
1,1,3-tris(5-t-butyl-4-hydroxy-2-methylphenyl)-3-n-dodecylmercaptobutane,
ethylene glycol bis{3,3-bis(3'-t-butyl-4'-hydroxyphenyl)butyrate},
di(3-t-butyl-4-hydroxy-5-methylphenyl)dicyclopentadiene,
di{2-(3'-t-butyl-2'-hydroxy-5'-methylbenzyl)6-t-butyl-4-methylphenyl}terephthalate,
1,3,5-tris(3,5-di-t-butyl-4-hydroxybenzyl)2,4,6-trimethylbenzene,
di(3,5-di-t-butyl-4-hydroxybenzyl)sulfide,
3,5-di-t-butyl-4-hydroxybenzylmercaptoacetic acid isooctyl ester,
bis(4-t-butyl-3-hydroxy-2,6-dimethylbenzyl) dithioterephthalate,
1,3,5-tris(3,5-di-t-butyl-4-hydroxybenzyl)isocyanurate,
1,3,5-tris(4-t-butyl-3-hydroxy-2,6,dimethylbenzyl) isocyanurate,
3,5-di-t-butyl-4-hydroxybenzylphosphonic acid dioctadecyl ester,
3,5-di-t-butyl-4-hydroxybenzylphosphonic acid mono-ethyl ester calcium salt,
4-hydroxylauric acid anilide,
4-hydroxystearic acid anilide,
2,4-bis-octylmercapto-6-(3,5-di-t-butyl-4-hydroxyaniline)-s-triazine,
N-(3,5-di-t-butyl-4-hydroxyphenyl)carbamic acid octyl ester, and the like.

Another example of an antioxidant type that can be used in combination with the additives of the present invention are oil soluble copper compounds, and the like.

Examples of antiwear additives that can be used in combination with the additives of the present invention include organo borates, organo phosphites, organic sulfur-containing compounds, zinc dialkyl dithiophosphates, zinc diaryl dithiophosphates, phosphosulfurized hydrocarbon, and the like. The antiwear agents together with the secondary diarylamine type antioxidants in a lubricating oil provide a synergistic antioxidant mixture with the additives of the present invention. Suitable phosphates for use as antiwear agents include dihydrocarbyl dithiophosphates, wherein the hydrocarbyl groups contain an average of at least three carbon atoms. Particularly useful are metal salts of at least one dihydrocarbyl dithiophosphoric acid wherein the hydrocarbyl groups contain an average of at least three carbon atoms. The acids from which the dihydrocarbyl dithiophosphates can be derived can be illustrated by acids of the formula

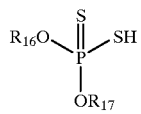

wherein $R_{16}$ and $R_{17}$ are the same or different and are alkyl, cycloalkyl, arakyl, alkaryl, or substituted substantially hydrocarbon radical derivatives or any of the above groups and wherein the $R_{16}$ and $R_{17}$ groups in the acid each have on average at least three carbon atoms. By "substantially hydrocarbon" is meant radicals containing substituent groups (e.g., one to four substituent groups per radical moiety) such as ether, ester, nitro, or halogen that do not materially affect the hydrocarbon character of the radical.

Specific examples of suitable $R_{16}$ and $R_{17}$ radicals include isopropyl, isobutyl, n-butyl, sec-butyl, n-hexyl, heptyl, 2-ethyl hexyl, diisobutyl, isooctyl, decyl, dodecyl, tetradecyl, hexadecyl, octadecyl, butylphenyl, o,p-dipentylphenyl, octylphenyl, polyisobutene-(molecular weight 350)-substituted phenyl, tetrapropylene-substituted phenyl, β-octylbutylnaphthyl, cyclopentyl, cyclohexyl, phenyl, chlorophenyl, o-dichlorophenyl, bromophenyl, naphthenyl, 2-methylcyclohexyl, benzyl, chlorobenzyl, chloropentyl, dichlorophenyl, nitrophenyl, dichlorodecyl, xenyl radicals, and the like. Alkyl radicals having from about 3 to about 30 carbon atoms and aryl radicals having about 6 to about 30 carbon atoms are preferred. Particularly preferred $R_{16}$ and $R_{17}$ radicals are alkyl of 4 to 18 carbon atoms.

The phosphorodithioic acids are readily obtainable by the reaction of phosphorus pentasulfide and an alcohol or phenol. The reaction involves mixing, at a temperature of about 20° C. to about 200° C., four moles of the alcohol or phenol with one mole of phosphorus pentasulfide. Hydrogen sulfide is liberated as the reaction takes place. Mixtures of alcohols, phenols, or both can be employed, e.g., mixtures of $C_3$ to $C_{30}$ alcohols, $C_6$ to $C_{30}$ aromatic alcohols, etc.

The metals useful to make the phosphate salts include Group I metals, Group II metals, aluminum, lead, tin, molybdenum, manganese, cobalt, and nickel. Zinc is the preferred metal. Examples of metal compounds that can be reacted with the acid include lithium oxide, lithium hydroxide, lithium carbonate, lithium pentylate, sodium oxide, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate, barium pentylate, aluminum oxide, aluminum prolylate, lead oxide, lead hydroxide, lead carbonate, tin oxide, tin butylate, cobalt oxide, cobalt hydroxide, cobalt carbonate, cobalt pentylate, nickel oxide, nickel hydroxide, nickel carbonate, and the like.

In some instances, the incorporation of certain ingredients, particularly carboxylic acids or metal carboxylates such as small amounts of the metal acetate or acetic acid used in conjunction with the metal reactant will facilitate the reaction and result in an improved product. For example, the use of up to about five percent of zinc acetate in combination with the required amount of zinc oxide facilitates the formation of a zinc phosphorodithioate.

The preparation of metal phosphorodithioates is well known in the art and is described in a large number of issued patents, including U.S. Pat. Nos. 3,293,181, 3,397,145, 3,396,109, and 3,442,804, the disclosures of which are incorporated herein by reference in their entirety.

Also useful as antiwear additives are amine derivatives of dithiophosphoric acid compounds such as are described in U.S. Pat. No. 3,637,499, the disclosure of which is incorporated herein by reference in its entirety.

The zinc salts are most commonly used as antiwear additives in lubricant oil in amounts of 0.1 to 10, preferably 0.2 to 2, weight percent, based upon the total weight of the lubricating oil composition. They may be prepared in accordance with known techniques by first forming a dithiophosphoric acid, usually by reaction of an alcohol or a phenol with $P_2S_5$, and then neutralizing the dithiophosphoric acid with a suitable zinc compound.

Mixtures of alcohols may be used including mixtures of primary and secondary alcohols, secondary generally for imparting improved antiwear properties, and primary for thermal stability. Mixtures of the two are particularly useful. In general, any basic or neutral zinc compound could be used, but the oxides, hydroxides, and carbonates are most generally employed. Commercial additives frequently contain an excess of zinc owing to the use of an excess of basic zinc compound in the neutralization reaction.

The zinc dihydrocarbyl dithiophosphates (ZDDP) are oil soluble salts of dihydrocarbyl esters of dithiophosphoric acids and may be represented by the following formula

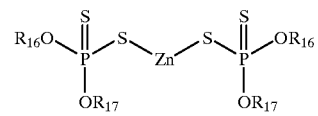

wherein $R_{16}$ and $R_{17}$ are as described in connection with the previous formula.

Compositions, when containing these additives, typically are blended into the base oil in amounts that are effective to provide their normal attendant function. Representative effective amounts of such additives are illustrated as follows:

| Compositions | Broad Weight % | Preferred Weight % |
| --- | --- | --- |
| V.I. Improver | 1–12 | 1–4 |
| Corrosion Inhibitor | 0.01–3 | 0.01–1.5 |
| Oxidation Inhibitor | 0.01–5 | 0.01–1.5 |
| Dispersant | 0.1–10 | 0.1–5 |
| Lube Oil Flow Improver | 0.01–2 | 0.01–1.5 |
| Detergents/Rust Inhibitors | 0.01–6 | 0.01–3 |
| Pour Point Depressant | 0.01–1.5 | 0.01–0.5 |
| Antifoaming Agents | 0.001–0.1 | 0.001–0.01 |
| Antiwear Agents | 0.001–5 | 0.001–1.5 |
| Seal Swellant | 0.1–8 | 0.1–4 |
| Friction Modifiers | 0.01–3 | 0.01–1.5 |
| Lubricating Base Oil | Balance | Balance |

When other additives are employed, it may be desirable, although not necessary, to prepare additive concentrates comprising concentrated solutions or dispersions of the subject additives of this invention (in concentrate amounts hereinabove described), together with one or more of the other additives (the concentrate when constituting an additive mixture being referred to herein as an additive-package) whereby several additives can be added simultaneously to the base oil to form the lubricating oil composition. Dissolution of the additive concentrate into the lubricating oil can be facilitated by solvents and by mixing accompanied by mild heating, but this is not essential. The concentrate or additive-package will typically be formulated to contain the additives in proper amounts to provide the desired concentration in the final formulation when the additive-package is combined with a predetermined amount of base lubricant. Thus, the subject additives of the present invention can be added to small amounts of base oil or other compatible solvents along with other desirable additives to form additive-packages containing active ingredients in collective amounts of typically about 2.5 to about 90 percent, and preferably about 15 to about 75 percent, and most preferably about 25 to about 60 percent by weight additives in the appropriate proportions with the remainder being base oil. The final formulations can employ typically about 1 to 20 weight percent of the additive-package with the remainder being base oil.

All of the weight percentages expressed herein (unless otherwise indicated) are based on active ingredient (AI) content of the additive and/or upon the total weight of any additive-package or formulation, which will be the sum of the AI weight of each additive plus the weight of total oil or diluent.

In general, the lubricant compositions of the present invention contain the additives in a concentration ranging from about 0.05 to about 30 weight percent. A concentration range for the additives ranging from about 0.1 to about 10 weight percent based on the total weight of the oil composition is preferred. A preferred concentration range is from about 0.2 to about 5 weight percent. Oil concentrates of the additives can contain about 1 to about 75 weight percent of the additive reaction product in a carrier or diluent oil of lubricating oil viscosity.

In general, the additives of the present invention are useful in a variety of lubricating oil basestocks. The lubricating oil basestock is any natural or synthetic lubricating base oil stock fraction having a kinematic viscosity at 100° C. of about 2 to about 200 cSt, more preferably about 3 to about 150 cSt, most preferably about 3 to about 100 cSt. The lubricating oil basestock can be derived from natural lubricating oils, synthetic lubricating oils, or mixtures thereof. Suitable lubricating oil basestocks include basestocks obtained by isomerization of synthetic wax and wax, as well as hydrocrackate basestocks produced by hydrocracking (rather than solvent extracting) the aromatic and polar components of the crude. Natural lubricating oils include animal oils, vegetable oils (e.g., rapeseed oils, castor oils, and lard oil), petroleum oils, mineral oils, and oils derived from coal or shale.

Synthetic oils include hydrocarbon oils and halo-substituted hydrocarbon oils such as polymerized and inter-polymerized olefins, alkylbenzenes, polyphenyls, alkylated diphenyl ethers, alkylated diphenyl sulfides as well as their derivatives, analogs, and homologs, and the like. Synthetic lubricating oils also include alkylene oxide polymers, interpolymers, copolymers, and derivatives thereof wherein the terminal hydroxyl groups have been modified by esterification, etherification, etc. Another suitable class of synthetic lubricating oils comprises the esters of dicarboxylic acids with a variety of alcohols. Esters useful as synthetic oils also include those made from $C_5$ to $C_{12}$ monocarboxylic acids and polyols and polyol ethers.

Silicon-based oils (such as the polyalkyl-, polyaryl-, polyalkoxy-, or polyaryloxy-siloxane oils and silicate oils) comprise another useful class of synthetic lubricating oils. Other synthetic lubricating oils include liquid esters of phosphorus-containing acids, polymeric tetrahydrofurans, polyalphaolefins, and the like.

The lubricating oil can be derived from unrefined, refined, rerefined oils, or mixtures thereof. Unrefined oils are obtained directly from a natural source or synthetic source (e.g., coal shale, or tar and bitumen) without further purification or treatment. Examples of unrefined oils include a shale oil obtained directly from a retorting operation, a petroleum oil obtained directly from distillation, or an ester oil obtained directly from an esterification process, each of which is then used without further treatment. Refined oils are similar to the unrefined oils except that refined oils have been treated in one or more purification steps to improve one or more properties. Suitable purification techniques include distillation, hydrotreating, dewaxing, solvent extraction, acid or base extraction, filtration, and percolation, all of which are known to those skilled in the art. Rerefined oils are obtained by treating refined oils in processes similar to those used to obtain the refined oils. These rerefined oils are also known as reclaimed or reprocessed oils and often are additionally processed by techniques for removal of spent additives and oil breakdown products.

Lubricating oil base stocks derived from the hydroisomerization of wax can is also be used, either alone or in combination with the aforesaid natural and/or synthetic base stocks. Such wax isomerate oil is produced by the hydroisomerization of natural or synthetic waxes or mixtures thereof over a hydroisomerization catalyst. Natural waxes are typically the slack waxes recovered by the solvent dewaxing of mineral oils; synthetic waxes are typically the wax produced by the Fisher-Tropsch process. The resulting isomerate product is typically subjected to solvent dewaxing and fractionation to recover various fractions of specific viscosity range. Wax isomerate is also characterized by processing very high viscosity indices, generally having a VI of at least 130, preferably at least 135 and higher, and, following dewaxing, a pour point of about −20° C. and higher.

The additives of the present invention are especially useful as components in many different lubricating oil compositions. The additives can be included in a variety of oils with lubricating viscosity, including natural and synthetic lubricating oils and mixtures thereof. The additives can be included in crankcase lubricating oils for spark-ignited and compression-ignited internal combustion engines. The compositions can also be used in gas engine lubricants, turbine lubricants, automatic transmission fluids, gear lubricants, compressor lubricants, metal-working lubricants, hydraulic fluids, and other lubricating oil and grease compositions. The additives can also be used in motor fuel compositions.

The advantages and the important features of the present invention will be more apparent from the following examples.

EXAMPLE 1

Corn oil/N-methyl-1,3-propanediamine

Into a 500 ml four-neck flask were charged 350 grams (0.39 mole) of corn oil and 50 grams (0.58 mole) of N-methyl-1,3-propanediamine. The reaction media were heated to 115° C. under a nitrogen blanket with stirring, and this temperature was maintained for five hours. The reaction media were cooled to room temperature whereupon a quantity of 100 grams (0.14 mole) of this material was transferred to a 250 ml four-neck flask. This was followed by the addition of 50 grams of isopropyl alcohol. To this portion of the reaction intermediate a quantity of 12.1 grams (0.16 mole) of carbon disulfide was added slowly under a nitrogen blanket with stirring, which resulted in an exotherm requiring external cooling to maintain the reaction media temperature below 30° C. Then, 10.0 grams (0.07 mole) of molybdenum trioxide was added all at once, and the temperature was raised to 50° C. for one hour, then to 80° C. for three hours. The reaction media were then cooled to room temperature and diluted with 100 ml of hexane. This solution was then filtered through a bed of Celite filter aid. The hexane was then stripped off under vacuum to yield a dark reddish-brown liquid containing 6.3 weight percent molybdenum and 3.1 weight percent sulfur.

EXAMPLE 2

Canola (Rapeseed) oil/N-methyl-1,3-propanediamine

Into a 500 ml four-neck flask were charged 350 grams (0.36 mole) of canola oil and 46 grams (0.54 mole) of N-methyl-1,3-propanediamine. The reaction media were heated to 117° C. under a nitrogen blanket with stirring, and this temperature was maintained for five hours. The reaction media were cooled to room temperature whereupon a quantity of 100 grams (0.14 mole) of this material was transferred to a is 250 ml four-neck flask. This was followed by the addition of 50 grams of isopropyl alcohol. To this portion of the reaction intermediate a quantity of 12.1 grams (0.16 mole) of carbon disulfide was added slowly under a nitrogen blanket with stirring, which resulted in an exotherm requiring external cooling to maintain the reaction media temperature below 30° C. Then 10.0 grams (0.07 mole) of molybdenum trioxide was added all at once, and the temperature was raised to 50° C. for one hour, then to 80° C. for three hours. The reaction media were then cooled to room temperature and diluted with 100 ml of hexane. This solution was then filtered through a bed of Celite filter aid. The hexane was then stripped off under vacuum to yield a dark reddish-brown liquid.

EXAMPLE 3

Canola (Rapeseed) oil/2-(2-aminoethyl)aminoethanol

Into a 500 ml four-neck flask were charged 350 grams (0.36 mole) of canola oil and 56 grams (0.54 mole) of N-methyl-1,3-propanediamine. The reaction media were heated to 117° C. under a nitrogen blanket with stirring, and the temperature was maintained for five hours. The reaction media were cooled to room temperature whereupon a quantity of 100 grams (0.14 mole) of this material was transferred to a 250 ml four-neck flask. This was followed by the addition of 50 grams of isopropyl alcohol. To this portion of the reaction intermediate a quantity of 13.0 grams (0.17 mole) of carbon disulfide was added slowly under a nitrogen blanket with stirring, which resulted in an exotherm requiring external cooling to maintain the reaction media temperature below 30° C. Then a quantity of 10.5 grams (0.073 mole) of molybdenum trioxide was added all at once, and the temperature was raised to 50° C. for one hour, then to 95° C. for one hour. The reaction media were then cooled to room temperature and diluted with 100 ml of hexane. This solution was then filtered through a bed of Celite filter aid. The hexane was then stripped off under vacuum to yield a dark reddish-brown liquid.

EXAMPLE 4

Canola (Rapeseed) oil/N-methyl-1,3-propanediamine/No/$CS_2$ treatment

Into a 500 ml four-neck flask were charged 350 grams (0.36 mole) of canola oil and 47 grams (0.54 mole) of N-methyl-1,3-propanediamine. The reaction media were heated to 117° C. under a nitrogen blanket with stirring, and the temperature was maintained for five hours. The reaction media were cooled to room temperature whereupon a quantity of 100 grams (0.14 mole) of this material was transferred to a 250 ml four-neck flask. This was followed by the addition of 50 grams of isopropyl alcohol. To this portion of the reaction intermediate a quantity of 10.5 grams (0.073 mole) of molybdenum trioxide was added all at once under a nitrogen blanket with stirring, and the temperature was raised to 88° C. for three hours, then cooled to room temperature. The mixture was diluted with 100 ml of hexane. This solution was then filtered through a bed of Celite filter aid. The hexane was then stripped off under vacuum.

EXAMPLE 5

Repeat of Example 2, Canola (Rapeseed) oil/N-methyl-1,3-propanediamine

Into a 500 ml four-neck flask were charged 350 grams (0.36 mole) of canola oil and 47 grams (0.54 mole) of N-methyl-1,3-propanediamine. The reaction media were heated to 117° C. under a nitrogen blanket with stirring, and the temperature was maintained for five hours. The reaction media were cooled to room temperature whereupon a quantity of 180 grams (0.24 mole) of this material was transferred to a 500 ml four-neck flask. This was followed by the addition of 90 grams of isopropyl alcohol. To this portion of the reaction intermediate a quantity of 22.3 grams (0.29 mole) of carbon disulfide was added slowly under a nitrogen blanket with stirring,, which resulted in an exotherm requiring external cooling to maintain the reaction media temperature below 30° C. Then 18.0 grams (0.12 mole) of molybdenum trioxide was added all at once, and the temperature was raised to 50° C. for one hour, then to 87° C. for five hours. The reaction media were then cooled to room temperature and diluted with 200 ml of hexane. This solution was then filtered through a bed of Celite filter aid. The hexane was then stripped off under vacuum to yield a dark reddish-brown liquid.

EXAMPLE 6

Canola oil/N-cyclohexylpropanediamine

Into a 500 ml four-neck flask were charged 350 grams (0.36 mole) of canola oil and 84 grams (0.54 mole) of N-cyclohexyl-1,3-propanediamine. The reaction media were heated to 117° C. under a nitrogen blanket with stirring, and the temperature was maintained for five hours. The reaction media were cooled to room temperature whereupon 100 grams (0.12 mole) of this material was transferred to a 250 ml four-neck flask. This was followed by the addition of 50 grams of isopropyl alcohol. To this portion of the reaction intermediate a quantity of 12 grams (0.15 mole) of carbon disulfide was added slowly under a nitrogen blanket with stirring, which resulted in an exotherm requiring external cooling to maintain the reaction media temperature below 30° C. Then 8.8 grams (0.06 mole) of molybdenum trioxide was added all at once, and the temperature raised to 50° C. for one hour, then to 100° C. for one hour. The reaction temperature was then raised to 120° C. for one hour, then to 135° C. for four hours. The reaction media were then cooled to room temperature and diluted with 100 ml of hexane. This solution was then filtered through a bed of Celite filter aid. The hexane was then stripped off under vacuum to yield a dark reddish-brown liquid.

EXAMPLE 7

Canola (Rapeseed) oil/N-methyl-1,3-propanediamine/No IPA

Into a 250 ml four-neck flask were charged 125 grams (0.13 mole) of canola oil and 17 grams (0.19 mole) of N-methyl-1,3-propanediamine. Under a nitrogen blanket with stirring, the reaction media were heated to 120° C., and the temperature was maintained for five hours. The reaction media were cooled to room temperature whereupon a quantity of 8.2 grams (0.10 mole) of carbon disulfide was added slowly under a nitrogen blanket with stirring, which resulted in an exotherm requiring external cooling to maintain the reaction media temperature below 36° C. Then 12.1 grams (0.085 mole) of molybdenum trioxide was added all at once, and the temperature was raised to 80° C. for two and one-half hours, then to 125° C. for two hours. The reaction media were then cooled to room temperature and diluted with 80 ml of hexane. This solution was then filtered through a bed of Celite filter aid. The hexane was then stripped off under vacuum to yield a dark reddish-brown liquid.

EXAMPLE 8

Into a one-liter four-neck flask were charged 500 grams (0.52 mole) of canola oil and 68 grams (0.76 mole) of N-methyl-1,3-propanediamine. The reaction media were heated to 120° C. under a nitrogen blanket with stirring, and the temperature was maintained for five hours. The reaction media were cooled to room temperature whereupon a quantity of 34.2 grams (0.45 mole) of carbon disulfide was added slowly under a nitrogen blanket with stirring, which resulted in an exotherm requiring external cooling to maintain the reaction media temperature below 36° C. Then 50 grams (0.35 mole) of molybdenum trioxide was added all at once, and the temperature was raised to 90° C. for one hour, then to 120° C. for six and one-half hours. The reaction media were then cooled to room temperature and diluted with 600 ml of hexane. This solution was then filtered through a bed of Celite filter aid. The hexane was then stripped off under vacuum to yield a dark reddish-brown liquid.

EXAMPLE 9

Into a one-liter four-neck flask were charged 475 grams (0.49 mole) of canola oil and 64 grams (0.72 mole) of N-methyl-1,3-propanediamine. The reaction media were heated to 120° C. under a nitrogen blanket with stirring, and the temperature was maintained for six hours. The reaction media were cooled to room temperature whereupon a quantity of 29.6 grams (0.39 mole) of carbon disulfide was added slowly under a nitrogen blanket with stirring, which resulted in an exotherm requiring external cooling to maintain the reaction media temperature below 36° C. Then 46 grams (0.33 mole) of molybdenum trioxide was added all at once, and the temperature was raised to 82° C. for two hours, then to 125° C. for three hours. The reaction media were then cooled to room temperature and diluted with 400 ml of hexane. This solution was then filtered through a bed of Celite filter aid. The hexane was then stripped off under vacuum to yield a dark reddish-brown liquid.

EXAMPLE 10

Canola oil/N-isopropyl-1,3-propanediamine

Into a 250 ml four-neck flask were charged 85 grams (0.088 mole) of canola oil and 15 grams (0.13 mole) of N-isopropyl-1,3-propanediamine. The reaction media were heated to 120° C. under a nitrogen blanket with stirring, and the temperature was maintained for six hours. The reaction media were cooled to room temperature whereupon a quantity of 5.4 grams (0.071 mole) of carbon disulfide was added slowly under a nitrogen blanket with stirring, which resulted in an exotherm requiring external cooling to maintain the reaction media temperature below 36° C. Then 8.6 grams (0.06 mole) of molybdenum trioxide was added all at once, and the temperature was raised to 80° C. for one hour, then to 125° C. for three hours. The reaction media were then cooled to room temperature and diluted with 100 ml of hexane. This solution was then filtered through a bed of Celite filter aid. The hexane was then stripped off under vacuum to yield a dark reddish-brown liquid.

EXAMPLE 11

Soya oil/N-methyl-1,3-propanediamine

Into a one-liter four-neck flask were charged 328 grams (0.49 mole) of Soya oil and 64 grams (0.72 mole) of N-methyl-1,3-propanediamine. The reaction media i s were heated to 120° C. under a nitrogen blanket with stirring, and the temperature was maintained for six hours. The reaction media were cooled to room temperature whereupon a quantity of 29.6 grams (0.39 mole) of carbon disulfide was added slowly under a nitrogen blanket with stirring, which resulted in an exotherm requiring external cooling to maintain the reaction media temperature below 36° C. Then 44 grams (0.31 mole) of molybdenum trioxide was added all at once, and the temperature was raised to 80° C. for one hour, then to 125° C. for one hour. The reaction media were then cooled to room temperature and diluted with 450 ml of hexane. This solution was then filtered through a bed of Celite filter aid. The hexane was then stripped off under vacuum to yield a dark reddish-brown liquid.

EXAMPLE 12

Similar repeat of Example 7

Into a three-liter four-neck flask were charged 950 grams (0.98 mole) of canola oil and 128 grams (0.1.44 moles) of N-methyl-1,3-propanediamine. The reaction media were heated to 120° C. under a nitrogen blanket with stirring, and the temperature was maintained for six hours. The reaction media were cooled to room temperature whereupon a quantity of 60 grams (0.78 mole) of carbon disulfide was added slowly under a nitrogen blanket with stirring, which resulted in an exotherm requiring external cooling to maintain the reaction media temperature below 36° C. Then 92 grams (0.66 mole) of molybdenum trioxide was added all at once, and the temperature was raised to 80° C. for one hour, then to 125° C. for one and one-half hours. The reaction media were then cooled to room temperature and diluted with 800 ml of hexane. This solution was then filtered through a bed of Celite filter aid. The hexane was then stripped off under vacuum to yield a dark reddish-brown liquid.

EXAMPLE 13

Safflower oil/N-methyl-1,3-propanediamine

Into a 250 ml four-neck flask were charged 77.8 grams (0.88 mole) of safflower oil and 11.4 grams (0.13 mole) of N-methyl-1,3-propanediamine. The reaction media were heated to 120° C. under a nitrogen blanket with stirring, and the temperature was maintained for six hours. The reaction media were cooled to room temperature whereupon a quantity of 5.4 grams (0.071 mole) of carbon disulfide was added slowly under a nitrogen blanket with stirring, which resulted in an exotherm requiring external cooling to maintain the reaction media temperature below 36° C. Then 8.6 grams (0.06 mole) of molybdenum trioxide was added all at once, and the temperature was raised to 80° C. for one hour, then to 125° C. for one hour. The reaction media were then cooled to 90° C., then filtered through a bed of Celite filter aid to yield a dark reddish-brown liquid.

EXAMPLE 14

Canola oil/Iododecyloxypropyl-1,3-diaminopropane

Into a 250 ml four-neck flask were charged 75 grams (0.78 mole) of Canola oil and 37 grams (0.114 mole) of isododecyloxypropyl-1,3-diaminopropane. The reaction media were heated to 130° C. under a nitrogen blanket with stirring, and the temperature was maintained for 11.5 hours. The reaction media were cooled to room temperature whereupon a quantity of 4.6 grams (0.06 mole) of carbon disulfide was added slowly under a nitrogen blanket with stirring, which resulted in an exotherm requiring external cooling to maintain the reaction media temperature below 36° C. Then 7.0 grams (0.049 mole) of molybdenum trioxide was added all at once, and the temperature was raised to 80° C. for half an hour, then to 125° C. for one hour, followed by raising the temperature again to 130° C. for two hours. The reaction media were then cooled to 90° C., then filtered through a bed of Celite filter to yield a dark reddish-brown liquid.

EXAMPLE 15

Into a two-liter four-neck flask were charged 750 grams (0.78 mole) of Canola oil and 370 grams (01.14 moles) of isododecyloxypropyl-1,3-diaminopropane. The reaction media were heated to 130° C. under a nitrogen blanket with stirring, and the temperature was maintained for nine hours. The reaction media were cooled to room temperature whereupon a quantity of 46 grams (0.6 mole) of carbon disulfide was added slowly under a nitrogen blanket with stirring, which resulted in an exotherm requiring external cooling to maintain the reaction media temperature below 36° C. Then 70 grams (0.49 mole) of molybdenum trioxide was added all at once, and the temperature was raised to 105° C. for half an hour, then to 135° C. for three hours. The reaction media were then cooled to 75° C., then filtered through a bed of Celite filter aid to yield a dark reddish-brown liquid.

EXAMPLE 16

Into a two-liter four-neck flask were charged 750 grams (0.78 mole) of Canola oil and 370 grams (01.14 mole) of isododecyloxypropyl-1,3-diaminopropane. The reaction media were heated to 135° C. under a nitrogen blanket with stirring, and the temperature was maintained for seven hours. The reaction media were cooled to room temperature whereupon a quantity of 46 grams (0.6 mole) of carbon disulfide was added slowly under a nitrogen blanket with stirring, which resulted in an exotherm requiring external cooling to maintain the reaction media temperature below 36° C. Then 70 grams (0.49 mole) of molybdenum trioxide was added all at once, and the temperature was raised to 105° C. for 45 minutes, then to 135° C. for three hours. The reaction media were then cooled to 75° C., then filtered through a bed of Celite filter aid to yield a dark reddish-brown liquid.

EXAMPLE 17

Canola Oil/N-oleyl-1,3-propanediamine

Into a 250 ml four-neck flask were charged 75 grams (0.078 mole) of canola oil and 41 grams (0.117 mole) of N-oleyl-1,3-propanediamine. The reaction media were heated to 135° C. under a nitrogen blanket with stirring, and the temperature was maintained for nine hours. The reaction media were cooled to room temperature whereupon a quantity of 4.5 grams (0.058 mole) of carbon disulfide was added slowly under a nitrogen blanket with stirring, which resulted in an exotherm requiring external cooling to maintain the reaction media temperature below 36° C. Then 7.0 grams (0.049 mole) of molybdenum trioxide was added all at once, and the temperature was raised to 109° C. for half an hour, then to 135° C. for three hours. The reaction media were then cooled to 70° C., then filtered through a bed of Celite filter aid to yield a dark reddish-brown liquid.

EXAMPLE 18

Canola oil/N-methyl-1,3-propanediamine, similar to Example 13

Into a three-liter four-neck flask were charged 1250 grams (1.27 moles) of canola oil and 166 grams (0.188 mole) of N-methyl-1,3-propanediamine. The reaction media were heated to 120° C. under a nitrogen blanket with stirring, and the temperature was maintained for six hours. The reaction media were cooled to room temperature whereupon a quantity of 78 grams (1.01 moles) of carbon disulfide was added slowly under a nitrogen blanket with stirring, which resulted in an exotherm requiring external cooling to maintain the reaction media temperature below 36° C. Then 117 grams (0.83 mole) of molybdenum trioxide was added all at once, and the temperature was raised to 80 to 85° C. for half an hour, then to 125° C. for one hour. The reaction media were then cooled to 80° C., then filtered through a bed of Celite filter aid to yield a dark reddish-brown liquid.

EXAMPLE 19

Corn oil/Octyl/decyloxypropyl-1,3-diaminopropane

Into a 250 ml four-neck flask were charged 69 grams (0.078 mole) of corn oil and 33 grams (0.114 mole) of octyl/decyloxypropyl-1,3-diaminopropane. The reaction media were heated to 130° C. under a nitrogen blanket with stirring, and the temperature was maintained for nine hours. The reaction media were cooled to room temperature whereupon a quantity of 4.6 grams (0.06 mole) of carbon disulfide was added slowly under a nitrogen blanket with stirring, which resulted in an exotherm requiring external cooling to maintain the reaction media temperature below 36° C. Then 70 grams (0.049 mole) of molybdenum trioxide was added all at once, and the temperature was raised to 105° C. for half an hour, then to 135° C. for three hours. The reaction media were then cooled to 65° C., then filtered through a bed of Celite filter aid to yield a dark reddish-brown liquid.

EXAMPLE 20

Canola oil/N-methyl-1,3-propanediamine/No/CS2/Molybdenum

Into a 500 ml four-neck flask were charged 350 grams (0.36 mole) of canola oil and 47 grams (0.54 mole) of N-methyl-1,3-propanediamine. The reaction media were heated to 117° C. under a nitrogen blanket with stirring, and the temperature was maintained for five hours. The reaction product was then cooled to room temperature.

Cameron-Plint TE77 High Frequency Friction Machine Friction Coefficient Testing The antifriction properties of the novel reaction product in a fully formulated lubricating oil were determined in the Cameron Plint TE77 Friction Test. The fully formulated lubricating oils tested contained one weight percent of the additive to be tested. The additives were tested for effectiveness in a motor oil at increasing temperature points and compared to identical formulations with and without the friction. In Table 1, the numerical value of the test results Plate (RC 60/0.4 micron). A reciprocating specimen, a 16 mm long nitrided steel dowel pin (6 mm diameter, 60 Rc) is placed on top of the steel plate under a 50 Newton load, allowed to heat up to 35° C. from room temperature over ten minutes, and maintained at 35° C. for five minutes. Then, with the 50 Newton load in place, the reciprocation frequency of 5 Hertz is begun with a 15 millimeter amplitude stroke length. The temperature is then ramped up to 50° C. over ten minutes and maintained at 50° C. for five minutes. The load is then increased to 100 Newtons, and the temperature is ramped up to 165° C. over one hour. Friction Coefficient data is collected between 600 to 160° C. The flat specimen is cleaned between runs with hexanes and #500 emery cloth. A new dowel pin or surface of the dowel pin is used each time. A reference oil is run alternately between experimental oils. The same flat specimen is used until the reference oil no longer provides reproducible results.

The motor oil formulation tested is an SAE 10W-30 grade containing dispersant, detergent, antioxidant, rust inhibitor, pour point depressant, OCP VI improver, and antiwear additive. Friction modifier was added as a top treat to this formula.

TABLE 1

Cameron-Plint TE77 High Frequency Friction Machine Results
Coefficient of Friction at Temperature, ° C.

| Example | Wt. % | 60° C. | 80° C. | 100° C. | 120° C. | 140° C. | 160° C. |
|---|---|---|---|---|---|---|---|
| No FM[1] | 0.0 | 0.125 | 0.128 | 0.128 | 0.120 | 0.115 | 0.100 |
| 1 | 1.0 | 0.055 | 0.045 | 0.040 | 0.045 | 0.045 | 0.043 |
| 2 | 1.0 | 0.040 | 0.040 | 0.040 | 0.040 | 0.040 | 0.040 |
| 2 | 0.5 | 0.038 | 0.040 | 0.040 | 0.038 | 0.035 | 0.035 |
| 2 | 0.3 | 0.068 | 0.040 | 0.045 | 0.050 | 0.045 | 0.040 |
| 3 | 1.0 | 0.115 | 0.116 | 0.115 | 0.100 | 0.075 | 0.055 |
| 4 | 1.0 | 0.115 | 0.090 | 0.050 | 0.035 | 0.030 | 0.035 |
| 5 | 0.3 | 0.118 | 0.070 | 0.055 | 0.063 | 0.060 | 0.055 |
| 5 | 1.0 | 0.088 | 0.030 | 0.039 | 0.053 | 0.053 | 0.049 |
| 6 | 1.0 | 0.120 | 0.053 | 0.033 | 0.035 | 0.038 | 0.035 |
| 7 | 1.0 | 0.040 | 0.047 | 0.058 | 0.063 | 0.055 | 0.043 |
| 9 | 1.0 | 0.040 | 0.038 | 0.038 | 0.048 | 0.047 | 0.038 |
| 10 | 1.0 | 0.035 | 0.033 | 0.036 | 0.040 | 0.035 | 0.035 |
| 11 | 1.0 | 0.029 | 0.033 | 0.035 | 0.036 | 0.037 | 0.035 |
| 12 | 1.0 | 0.033 | 0.035 | 0.056 | 0.060 | 0.058 | 0.043 |
| 13 | 1.0 | 0.280 | 0.035 | 0.048 | 0.062 | 0.063 | 0.050 |
| 14 | 0.5 | 0.120 | 0.117 | 0.117 | 0.100 | 0.080 | 0.065 |
| 14 | 1.0 | 0.098 | 0.035 | 0.030 | 0.030 | 0.035 | 0.032 |
| 14 | 1.5 | 0.065 | 0.035 | 0.028 | 0.033 | 0.040 | 0.038 |
| 15 | 1.0 | 0.045 | 0.038 | 0.040 | 0.050 | 0.062 | 0.042 |
| 16 | 1.0 | 0.045 | 0.032 | 0.035 | 0.035 | 0.035 | 0.035 |
| 17 | 1.0 | 0.060 | 0.035 | 0.030 | 0.033 | 0.040 | 0.043 |
| 18 | 1.0 | 0.035 | 0.030 | 0.033 | 0.056 | 0.040 | 0.035 |
| 19 | 0.5 | 0.050 | 0.033 | 0.035 | 0.036 | 0.040 | 0.039 |
| 19 | 1.0 | 0.028 | 0.028 | 0.034 | 0.040 | 0.037 | 0.035 |
| 19 | 1.5 | 0.030 | 0.03 | 0.034 | 0.045 | 0.053 | 0.043 |
| 20 (No Mo) | 1.0 | 0.115 | 0.108 | 0.107 | 0.108 | 0.112 | 0.115 |
| CFM[2] (No Mo) | 1.0 | 0.115 | 0.118 | 0.115 | 0.115 | 0.121 | 0.121 |

[1]The reference oil is a fully formulated 10W-30 gasoline crank case motor oil containing no friction modifier.
[2]CFM is an ashless commercially available friction modifier based upon a mixture of fatty acid amides, glycerol esters, and glycerol.

(Coefficient of Friction) decreases with an increase in effectiveness. In other words, the lower the friction coefficient value, the better the additive is at reducing friction.

The test procedure for determining the friction coefficient with the Cameron-Plint TE77 High Frequency Friction Machine is as follows. A quantity of 10 ml of an oil sample containing the additive is placed in the test chamber so as to cover a flat, stationary, hardened ground NSOH B01 Gauge

Falex Four-Ball Antiwear Testing

The antiwear properties of the novel reaction product in a fully formulated lubricating oil were determined in the Four-Ball Wear Test under the ASTM D 4172 test conditions. The fully formulated lubricating oils tested also contained one weight percent cumene hydroperoxide to help simulate the environment within a running engine. The additives were tested for effectiveness in two motor oil formulations (See description in Table 2) and compared to identical formulations with and without any zinc dialkyldithiophosphate. In Table 3 the numerical value of the test results (Average Wear Scar Diameter, mm) decreases with an increase in effectiveness.

TABLE 2

SAE 10W-30 Motor Oil Formulations

| Formulation A | wt. % | Formulation B | wt. % |
|---|---|---|---|
| Solvent Neutral 100 | Balance | Solvent Neutral 100 | Balance |
| Solvent Neutral 150 | 60 | Solvent Neutral 150 | 60 |
| Succinimide Dispersant | 7.5 | Succinimide Dispersant | 7.5 |
| Overbased Calcium Phenate Detergent | 2.0 | Overbased Calcium Sulfonate Detergent | 2.0 |
| Rust/Corrosion Inhibitor | 0.6 | Rust/Corrosion Inhibitor | 0.6 |
| Antioxidant | 0.5 | Antioxidant | 0.5 |
| Pour Point Depressant | 0.1 | Pour Point Depressant | 0.1 |
| OCP VI Improver | 5.5 | OCP VI Improver | 5.5 |
| Antiwear Additive[1] | 1.0 | Antiwear Additive | 1.0 |

[1]In the case of No antiwear additive in Table 3, solvent neutral 100 is put in its place at 1.0 weight percent. The formulation is treated so that 1 weight percent antiwear additive is based upon 100 percent active material. For the examples in Tables 3 and 4 with zinc dialkyldithiophosphate (ZDDP), the ZDDP is the antiwear additive in these cases.

TABLE 3

Falex Four-Ball Wear Results

| Example | Formulation | Wear Scar Diameter, mm |
|---|---|---|
| No antiwear additive | A | 0.93 |
| Zinc dialkyldithiophosphate | A | 0.46 |
| 1 | A | 0.55 |
| 2 | A | 0.71 |
| 4 | A | 0.54 |
| 5 | A | 0.57 |
| 7 | A | 0.64 |
| 9 | A | 0.49 |
| 10 | A | 0.74 |
| 11 | A | 0.77 |
| 12 | A | 0.64 |
| 13 | A | 0.46 |
| 14 | A | 0.60 |
| 15 | A | 0.57 |
| 16 | A | 0.68 |
| 19 | A | 0.59 |
| No antiwear additive | B | 0.98 |
| Zinc dialkyldithiophosphate | B | 0.53 |
| 1 | B | 0.57 |
| 2 | B | 0.56 |
| 3 | B | 0.55 |
| 5 | B | 0.65 |
| 6 | B | 0.76 |
| 7 | B | 0.44 |
| 9 | B | 0.61 |
| 10 | B | 0.59 |
| 11 | B | 0.73 |
| 12 | B | 0.66 |
| 13 | B | 0.58 |
| 14 | B | 0.61 |
| 15 | B | 0.46 |
| 16 | B | 0.65 |
| 19 | B | 0.54 |

Cameron-Plint TE77 High Frequency Friction Machine Antiwear Testing

The antiwear properties of the additives of this invention in a fully formulated lubricating oil were determined in the Four-Ball Wear test under the ASTM D 4172 test conditions. The specimen parts (6 mm diameter AISI 52100 steel ball of 800± 20 kg/mm² hardness and hardened ground NSOH B01 gauge plate of RC 60/0.4 micron) were rinsed and then sonicated for 15 minutes with technical grade hexanes. This procedure is repeated with isopropyl alcohol. The specimens were dried with nitrogen and set into the TE77. The oil bath was filled with 10 ml of sample. The test was run at a 30 Hertz Frequency, 100 Newton Load, 2.35 mm Amplitude. The test stared with the specimens and oil at room temperature. Immediately, the temperature was ramped over 15 minutes to 50° C., where it dwelled for 15 minutes. The temperature was then ramped over 15 minutes to 100° C., where it dwelled at 100° C. for 45 minutes. A third temperature ramp over 15 minutes to 150° C. was followed by a final dwell at 150° C. for 15 minutes. The total length of the test was two hours. At the end of the test, the wear scar diameter on the 6 mm ball was measured using a Leica StereoZoom6® Stereomicroscope and a Mitutoyo 164 series Digimatic Head. The fully formulated lubricating oils tested contained one weight percent cumene hydroperoxide to help simulate the environment within a running engine. The additives were tested for effectiveness in two motor oil formulations (see formulation descriptions in Table 2) and compared to identical formulations with and without any zinc dialkyldithiophosphate. In Table 4, the numerical value of the test results (Wear Scar Diameter, mm) decreases with an increase in effectiveness.

TABLE 4

Cameron-Plint TE 77 High Frequency Friction Machine Wear Results

| Example | Formulation | Wear Scar Diameter, mm |
|---|---|---|
| No antiwear additive | A | 0.66 |
| Zinc dialkyldithiophosphate | A | 0.46 |
|  | A | 0.46 |
| 1 | A | 0.57 |
|  | A | 0.44 |
| 2 | A | 0.58 |
|  | A | 0.37 |
| 4 | A | 0.64 |
| 9 | A | 0.62 |
| 14 | A | 0.64 |
| 16 | A | 0.61 |
| 19 | A | 0.63 |
|  | A | 0.55 |
| No antiwear additive | B | 0.67 |
|  | B | 0.67 |
| Zinc dialkyldithiophosphate | B | 0.54 |
|  | B | 0.54 |
| 1 | B | 0.66 |
| 9 | B | 0.43 |
|  | B | 0.57 |
| 14 | B | 0.65 |
| 16 | B | 0.62 |

Four-Ball Extreme Pressure Testing

The extreme pressure (EP) properties of the additives of this invention in a lubricating oil were determined in the Four-Ball Weld Test under the ASTM D 2783 test conditions. The additives were blended into an ISO 46 Grade Group II base oil (Chevron RLOP 240 R) at the weight percents cited in Table 5. The higher the Load Wear Index and the higher the Weld Point, the better the result.

TABLE 5

Four-Ball Extreme Pressure Test Results

| Examples | Wt. % | Oil | Weld Point (Kg) | Load Wear Index |
|---|---|---|---|---|
| No Extreme Pressure Additive | 0 | ISO 46 | 100 | 16.8 |
| 14 | 1 | ISO 46 | 126 | 25.9 |

Pressure Differential Scanning Calorimetry (PDSC) Testing

The Pressure Differential Scanning Calorimetry (PDSC) data in Table 7 are a measure of the oxidation induction time (OE) of each blend. The PDSC conditions are in Table 6. All formulations were blended at 65° C. for 15 minutes under a nitrogen atmosphere. The PDSC method employs a steel bomb under pressure; the catalyst is oil-soluble iron derived from iron napththanate. At the start of a run, the PDSC cell is initially heated at a rate of 40° C./min to the isothermal temperature listed in each results table. The induction time is measured from the time the sample reaches its isothermal temperature until the enthalpy change is observed. The longer the oxidation induction time, the better the oxidation stability of the oil. The PSDC instrument used is a Mettler DSC27HP manufactured by Mettler-Toledo, Inc. The test has a repeatability of ±2.5 minutes with 95 percent confidence for OIT's less than 100 min. Each data point is the average of two runs on a single test blend.

The results in Table 7 demonstrate the unexpected stability imparted to the oil compositions by the addition of the molybdenum thiocarbamyl derivatives of this invention, particularly in combination with ZDDP and alkylated diphenylamine antioxidants.

TABLE 6

PDSC Test Parameters

| Test | PDSC |
|---|---|
| Temperature | Variable (see data tables) |
| O$_2$ Gas Pressure | 500 psi |
| Flow Through Cell | 100 ml/min. |
| Catalyst | 50 ppm Iron |
| Sample Holder | Open Aluminum Pan |
| Sample Size | 3 mg |
| Induction Time | Enthalpy Change |

TABLE 7

PDSC Oxidation Stability Test Results in PCMO SAE 10W-30 Formulation

| Example | Formulation | Wt. % Example | Wt. % ZDDP[2] | OIT, min |
|---|---|---|---|---|
| 9 | B[1] | 0.50 | 1.0 | 105.2 |
| 9 | B[1] | 0.50 | 0.0 | 93.1 |
| 14 | B[1] | 0.50 | 1.0 | 116.5 |
| 14 | B[1] | 0.50 | 0.0 | 89.6 |
| No Friction Modifier | B[1] | 0.0 | 1.0 | 62.2 |

TABLE 7-continued

PDSC Oxidation Stability Test Results in PCMO SAE 10W-30 Formulation

| Example | Formulation | Wt. % Example | Wt. % ZDDP[2] | OIT, min |
|---|---|---|---|---|
| No Friction Modifier | B[1] | 0.0 | 0.0 | 15.3 |
| No Friction Modifier | C[3] | 0.0 | 1.0 | 10.7 |

[1]Formula B plus given weight percent of example (friction modifier) in place of base oil. Antiwear additive in Formula B is 1.0 or 0.0 weight percent ZDDP, when ZDDP is 0.0 weight percent the balance is made up with base oil.
[2]Zinc dialkyldithiophosphate
[3]Formula B without ashless antioxidant In view of the many changes and modifications that can be made without departing from principles underlying the invention, reference should be made to the appended claims for an understanding of the scope of the protection to be afforded the invention.

What is claimed is:

1. A lubricating oil additive comprising the reaction product of
   (a) an unsaturated or saturated ester or acid,
   (b) a diamine of the formula:

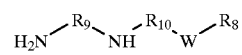

(c) carbon disulfide, and
   (d) a molybdenum compound selected from the group consisting of molybdic acid, ammonium molybdate, MoOCl$_4$, MoO$_2$Br$_2$, Mo$_2$O$_3$Cl$_6$, MoO$_3$, and the thio analogues of the foregoing, wherein R$_8$ is an alkyl group of 8 to 24 carbon atoms, R$_9$ and R$_{10}$ are independently selected aliphatic or aromatic moieties, and W is oxygen, sulfur, or —CH$_2$— and wherein (a) is first reacted with (b) to form a first reaction product, the first reaction product is then reacted with (c) to form a second reaction product, and the second reaction product is then reacted with (d) to form the final reaction product.

2. The additive of claim 1 wherein R$_9$ and R$_{10}$ are alkylene.

3. The additive of claim 1 wherein R$_9$ and R$_{10}$ are propylene.

4. The additive of claim 1 wherein W is oxygen.

5. The additive of claim 1 wherein the diamine is used in a concentration of about 10 weight percent to about 70 weight percent.

6. The additive of claim 1 comprising the molybdenum compound in a concentration of about 0.01 to about 15 weight percent.

7. The additive of claim 1 wherein the amine moiety is derived from octyl/decyloxypropyl-1,3-diaminopropane; isodecyloxypropyl-1,3-diaminopropane; isododecyloxypropyl-1,3-diaminopropane; dodecyl/tetradecyloxypropyl-1,3-diaminopropane; isotridecyloxypropyl-1,3-diaminopropane; tetradecyloxypropyl-1,3-diaminopropane; N-coco-1,3-diaminopropanes; N-tallow-1,3-diaminopropanes or N-oleyl-1,3-diaminopropane.

8. The additive of claim 1 wherein the unsaturated or saturated ester is vegetable oil.

9. A lubricating composition comprising a lubricating oil and an additive comprising the reaction product of
   a. an unsaturated or saturated ester or acid,
   b. a diamine of the formula:

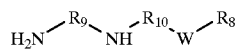

c. carbon disulfide, and
   d. a molybdenum compound selected from the group consisting of molybdic acid, ammonium molybdate, $MoOCl_4$, $MoO_2Br_2$, $Mo_2O_3$, and the thio analogues of the foregoing, wherein $R_8$ is an alkyl group of 8 to 24 carbon atoms, $R_9$ and $R_{10}$ are independently selected aliphatic or aromatic moieties, W is oxygen, sulfur, or —$CH_2$— and wherein (a) is first reacted with (b) to form a first reaction product, the first reaction product is then reacted with (c) to form a second reaction product, and the second reaction product is then reacted with (d) to form the final reaction product.

10. The additive of claim 9 wherein $R_9$ and $R_{10}$ are alkylene.

11. The additive of claim 9 wherein $R_9$ and $R_{10}$ are propylene.

12. The composition of claim 9 wherein W is oxygen.

13. The composition of claim 9 wherein the diamine is used in a concentration of about 10 weight percent to about 70 weight percent.

14. The composition of claim 9 comprising the molybdenum compound in a concentration of about 0.01 to about 15 weight percent.

15. The composition of claim 9 wherein the amine moiety is derived from octyl/decyloxypropyl-1,3-diaminopropane; isodecyloxypropyl-1,3-diaminopropane; isododecyloxypropyl-1,3-diaminopropane; dodecyl/tetradecyloxypropyl-1,3-diaminopropane; isotridecyloxypropyl-1,3-diaminopropane; tetradecyloxypropyl-1,3-diaminopropane; N-coco-1,3-diaminopropanes; N-tallow-1,3-diaminopropanes or N-oleyl-1,3-diaminopropane.

16. The composition of claim 9 wherein the unsaturated or saturated ester is vegetable oil.

17. The composition of claim 9 further comprising at least one additive selected from the group consisting of dispersants, detergents, corrosion/rust inhibitors, zinc dialkydithiophosphates, secondary aromatic amine antioxidants, hindered phenolic antioxidants, sulfur-containing hindered phenolic antioxidants, sulfurized olefins, thiadiazoles, VI improvers, and pour point depressants.

18. The composition of claim 17 wherein at least one additive is a secondary aromatic amine antioxidant of the formula $R_{11}$—NH—$R_{12}$ where $R_{11}$ and $R_{12}$ each independently represent a substituted or unsubstituted aryl group of 6 to 46 carbon atoms.

19. The composition of claim 18 where the secondary aromatic amine antioxidant is selected from the group consisting of diphenylamine, dialkylated diphenylamine, trialkylated diphenylamine, or mixtures thereof, 3-hydroxydiphenylamine, 4-hydroxydiphenylamine, N-phenyl-1,2-phenylenediamine, N-phenyl-1,4-phenylenediamine, mono- and/or di-butyldiphenylamine, mono- and/or di-octyldiphenylamine, mono- and/or di-nonyldiphenylamine, phenyl-α-naphthylamine, phenyl-β-naphthylamine, di-heptyldiphenylamine, mono- and/or di-(α-methylstyryl)diphenylamine, mono- and/or di-styryldiphenylamine, N,N'-diisopropyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethylbutyl)-N'-phenyl-p-phenylenediamine, N-(1-methylpentyl)-N'-phenyl-p-phenylenediamine, N-cyclohexyl-N'-phenyl-p-phenylenediamine, 4-(p-toluenesulfonamido) diphenylamine, 4-isopropoxydiphenylamine, tert-octylated N-phenyl-1-naphthylamino, and mixtures of mono- and dialkylated t-butyl-t-octyldiphenylamines.

20. The composition of claim 9 further comprising an additive selected from the group consisting of (a) secondary aromatic amine antioxidants of the formula $R_{11}$—NH—$R_{12}$ where $R_{11}$ and $R_{12}$ each independently represent a substituted or unsubstituted aryl group of 6 to 46 carbon atoms and (b) zinc dialkyl dithiophosphates.

21. The composition of claim 9 further comprising an additive selected from the group consisting of (a) secondary aromatic amine antioxidants of the formula $R_{11}$—NH—$R_{12}$ where $R_{11}$ and $R_{12}$ each independently represent a substituted or unsubstituted aryl is group of 6 to 46 carbon atoms and (b) zinc diaryl dithiophosphates.

* * * * *